US00PP09766P

United States Patent [19]

Harring

[11] Patent Number: Plant 9,766

[45] Date of Patent: Dec. 24, 1996

[54] GERANIUM PLANT NAMED 'HWD CORELLI'

[75] Inventor: Gabriele Harring, Kerpen, Germany

[73] Assignee: Dummen Jungpflanzenkulturen, Rheinberg-Eversael, Germany

[21] Appl. No.: 520,860

[22] Filed: Aug. 30, 1995

[30] Foreign Application Priority Data

May 16, 1988 [DE] Germany ..... PEL 308

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,969 9/1992 Hanes ..... Plt./87.12

*Primary Examiner*—James R. Feyrer

*Attorney, Agent, or Firm*—Proprietary Rights International

[57] ABSTRACT

A new and distinct cultivar of Geranium plant named HWD Corelli, characterized by its semi-double salmon-orange flowers; zonation pattern on foliage; and freely branching plant habit.

1 Drawing Sheet

The present invention relates to a new and distinct cultivar of Geranium plant, botanically known as *Pelargonium× hortorum,* known as the variety Duecorre, and hereinafter referred to by the cultivar name HWD Corelli.

The new cultivar is a product of a planned breeding program conducted by the inventor in Rheinberg, Germany. The objective of the breeding program was to develop a new semi-double geranium with salmon flowers and foliage with a zonation pattern.

The new cultivar originated from a cross made by the inventor of the proprietary selection 85-1-5 as the male or pollen parent with the proprietary selection 85-9-8 as the female or seed parent.

The cultivar HWD Corelli was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Corelli. These characteristics in combination distinguish HWD Corelli as a new and distinct cultivar:

1. Semi-double salmon-orange flowers.
2. Zonation pattern on foliage.
3. Freely branching plant habit.

In comparison to the parent selection 85–1–5, plants of the new Geranium are less vigorous and flowers are larger. In comparison to the parent selection 85-9-8, plants of the new Geranium have a more intense zonation pattern on the foliage, are more vigorous, have smaller flowers, and petal color is salmon and not orange.

The new Geranium is similar in petal color to the patented cultivar Designer Coral (U.S. Plant Pat. No. 8,522) and the cultivar HWD Gabrieli (disclosed in the inventor's pending application). In comparison to plants of the cultivar Designer Coral, plants of the New Geranium have shorter peduncles and a more intense zonation pattern on the foliage. In comparison to plants of the cultivar HWD Gabrieli, plants of the new Geranium have a more orange petal color, are more freely branching, more umbels per plant, fewer flowers per umbel, and longer peduncles.

The accompanying colored photograph illustrates the overall appearance of the new cultivar, showing the colors as true as it is reasonably possible to obtain in colored reproductions of this type. The photograph comprises a top perspective view of a typical potted plant of HWD Corelli with one plant in a 10-cm container.

The cultivar HWD Corelli has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperature of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical—Pelargonium×hortorum.*

*Commercial.*—Zonal Geranium.

*Cultivar.*—'HWD Corelli'.

Parentage:

*Male parent.*—Proprietary selection 85-1-5.

*Female parent.*—Proprietary selection 85-9-8.

Propagation:

*Type cutting.*—Terminal cuttings.

*Time to initiate roots.*—Summer: 27° C., 21 days; winter: 20° C., 28 days.

Plant description:

*General appearance.*—Rounded; medium plant size; upright; freely branching.

*Foliage description.*—Arrangement: Generally alternate. Shape: Orbicular with rounded tip and cordate base. Size: Length: 5 to 6.5 cm. Width: 5.5 to 7.5 cm. Texture: Velvety; pubescent on upper and under surfaces. Margin: Crenate. Color: Young foliage, upper surface: 147B. Young foliage, under surface: 147B. Mature foliage, upper surface: 147B. Mature foliage, under surface: 147B. Zonation pattern, upper surface: 147A. Veins, upper surface: 144A, not prominent. Veins, under surface: 144A. Petiole: 144A. Zonation: Width of zone: 1 to 1.5 cm. Location of zone: 0.5 cm from margin and 2.5 cm from petiole. Venation pattern: Palmate. Petiole: Length: 5 to 7.5 cm. Diameter: 2 to 2.5 mm.

*Stem description.*—Internode length: 1 to 1.5 cm. Stem color: 144A. Lateral branch number: 9. Lateral branch length: 6 to 7.5 cm.

Flowering description:

*Flowering habit.*—Freely flowering. Flowers arranged in umbels.

*Natural flowering season.*—Year-round.

*Flowers borne.*—Flower buds develop in apical leaf axils. Umbels are displayed above the foliage.

*Quantity of inflorescences.*—Very floriferous; usually 16 open umbels and at least 3 developing umbels per plant at one time.

*Imbels.*—Form: Rounded. Diameter: 11 cm. Depth (height): 7 to 8 cm.

*Flowers.*—Form: Semi-double. Shape: Rounded. Quantity of flowers per umbel: 28. Diameter: 4.5 cm. Depth (height): 2.3 cm.

*Petals.*—Shape: Obovate with rounded tip. Arrangement: Rosette, overlapping. Quantity: 5 to 6. Aspect: Flat. Size: Length: 2.5 to 2.7 cm. Width: 2.1 cm. Texture: Satiny, smooth. Margin: Entire. Color: When opening, upper surface: 52B to 41B. When opening, under surface: 36C and 41C. Upper surface: 40B. Under surface: 43C. Fading: Petal base fades to 155D.

*Petaloids.*—Shape: Irregular, generally obovate with rounded or clifted tip. Arrangement: Rosette, overlapping. Quantity: 5 to 7. Size: Length: 1.5 to 2 cm. Width: 1 to 1.5 cm. Texture: Satiny, smooth. Margin: Generally entire. Color: When opening, upper surface: 52B to 41B. When opening, under surface: 36C and 41C. Upper surface: 40B. Under surface: 43C. Fading: Petal base fades to 155D.

*Peduncle (umbel stem).*—Angle: Erect, some slight bending. Length: 12 to 15 cm. Pubescence: Very fine. Color: 144A.

*Pedicel (individual flower stem).*—Angle: Erect, rigid. Length: 3.2 to 3.5 cm. Pubescence: Very fine. Color: 144A at base, 53A at apex.

*Flower bud.*—Shape: Ovoid. Length: 1.5 cm. Diameter: 8 mm. Color: 27C with 44C at edge.

*Sepals.*—Arrangement: Rosette. Quantity: 5. Size: Length: 1 cm. Width: 3 to 4 mm. Shape: Acuminate with apiculate tip. Texture: Velvety. Margin: Entire. Color: Upper surface: 182B at base fading to 144A at tip. Under surface: 183D at base fading to 144A at tip.

*Reproductive organs.*—Androecium: Stamen number: 7 to 8. Anther size: 2 mm. Anther color: 53B. Pollen color: 34B. Gynoecium: Pistil number: 1. Pistil length: 1 cm. Stigma shape: Decurrent. Stigma color: 39A. Style length: 4 mm. Style color: 49D.

*Ploidy level.*—Tetraploid.

Disease resistance: No fungal, bacterial nor viral problems observed.

Seed development: Seed production is very rarely observed.

It is claimed:

1. A new and distinct cultivar of Geranium plant named HWD Corelli, as illustrated and described.

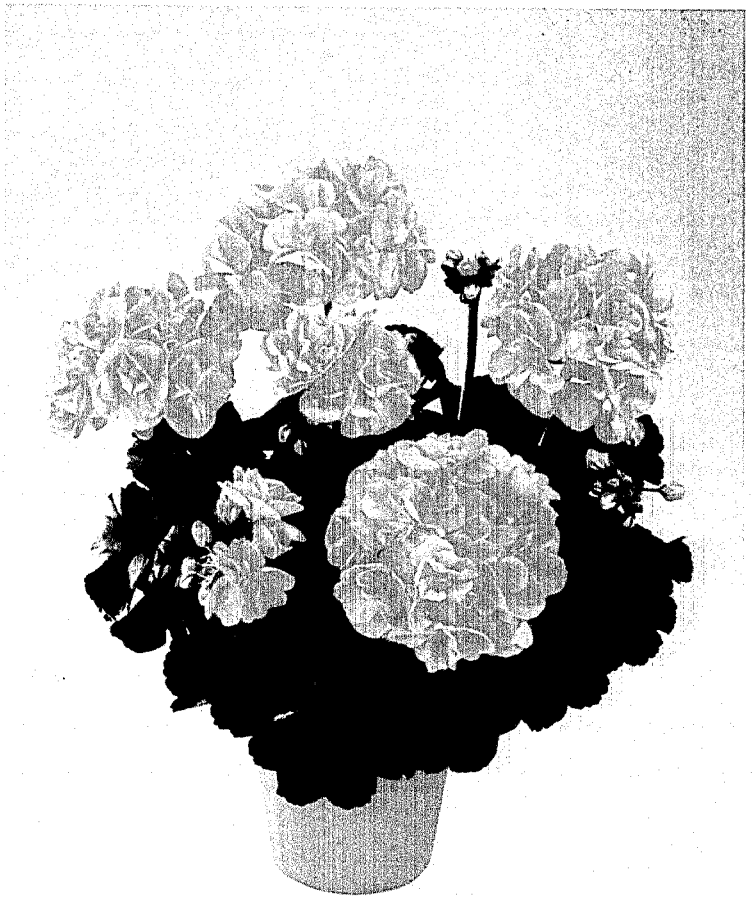

* * * * *